United States Patent [19]

Moore et al.

[11] Patent Number: 4,569,918
[45] Date of Patent: Feb. 11, 1986

[54] SULFUR DIOXIDE ANALYSIS SYSTEM

[75] Inventors: Robert T. Moore, Mountain View; Yoshihiro Takahashi, San Jose, both of Calif.

[73] Assignee: Xertex Corporation, Santa Clara, Calif.

[21] Appl. No.: 345,002

[22] Filed: Feb. 2, 1982

[51] Int. Cl.$^4$ .................. G01N 31/12; G01N 27/06
[52] U.S. Cl. .................... 436/122; 422/80; 422/88; 422/90; 436/150; 436/158; 436/175; 436/178
[58] Field of Search .......... 436/122, 155, 158, 160, 436/175, 178, 150; 422/78, 80, 88, 90; 73/23

[56] References Cited

U.S. PATENT DOCUMENTS

| 2,760,922 | 8/1956 | Williams, Jr. ............... 261/78 A X |
| 3,004,071 | 10/1961 | Warner et al. ............... 436/150 X |
| 3,547,590 | 12/1970 | Cropper et al. .............. 436/150 X |
| 3,867,098 | 2/1975 | Gorkovenko et al. ......... 422/88 |
| 4,120,659 | 10/1969 | Cropper . | |
| 4,133,640 | 1/1979 | Clinton et al. ............... 422/78 X |
| 4,172,705 | 10/1979 | Castro et al. ................ 422/80 X |
| 4,191,541 | 3/1980 | Jenkins ....................... 422/88 X |
| 4,233,276 | 11/1980 | D'Souza . | |
| 4,325,907 | 4/1982 | Dembicki, Jr. et al. ....... 422/80 X |
| 4,409,336 | 10/1983 | Oita ............................ 436/158 X |

FOREIGN PATENT DOCUMENTS 0014748  7/1964  Japan ................................ 436/158

OTHER PUBLICATIONS

Oita, Analytical Chemistry, vol. 55, 1983, No. 14, pp. 2434–2436.
Lowell et al., Ind. Eng. Chem. Process Des. Develop. vol. 10, No. 3, 1971, pp. 384–390.
Oita, I. J., "Determination of Sub-ppm Levels of Sulfur", Abstract 119, American Chemical Society, Las Vegas, Nevada Meeting (Aug. 27, 1980).

Primary Examiner—Arnold Turk
Attorney, Agent, or Firm—Flehr, Hohbach, Test, Albritton & Herbert

[57] ABSTRACT

A sulfur dioxide-containing analysis stream, such as formed by the oxidative pyrolysis of a sulfur-containing liquid, is passed through a trapping medium comprising metal or metal oxide, preferably nickel oxide, wherein the sulfur dioxide is retained while the remainder of the gas flows through. Thereafter, the flow of analysis gas is discontinued and the trap zone is heated to release the sulfur dioxide, which is passed in an inert carrier gas stream through a sulfur dioxide detector such as a conductivity cell. Halides in the analysis stream are removed prior to trapping by being dissolved in an aqueous liquid in a scrubbing chamber. Such chamber is regenerated by vaporizing the halide-containing aqueous solution and venting it. Also, a system of the foregoing type including two traps and a single detector whereby two samples are alternately analyzed and trapped to reduce the overall analysis time.

9 Claims, 9 Drawing Figures

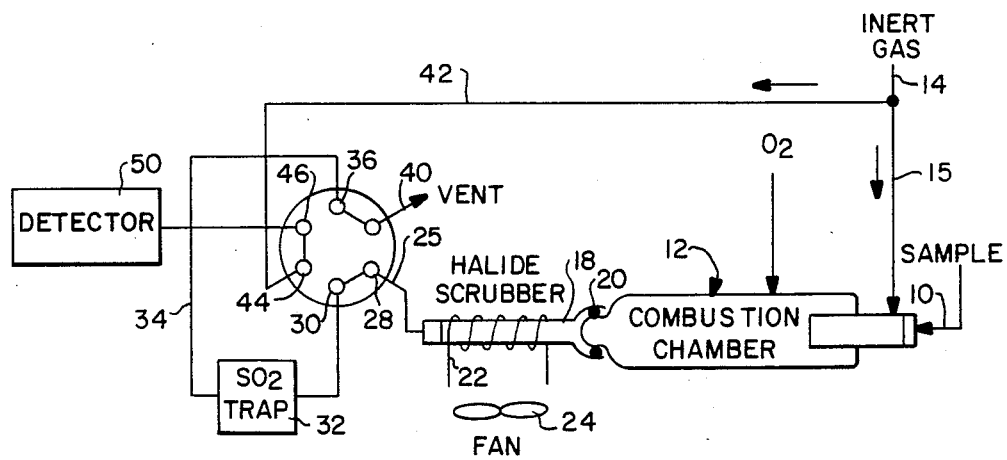
FIG.—1
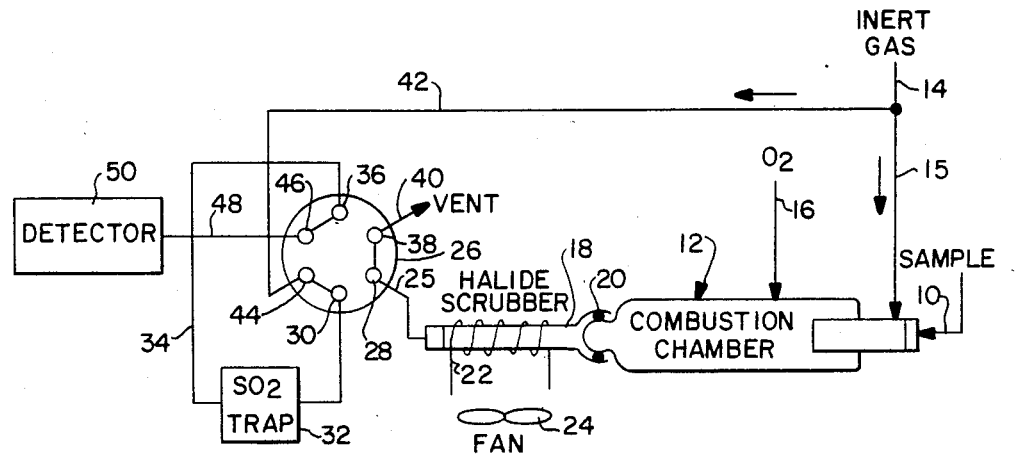
FIG.—2
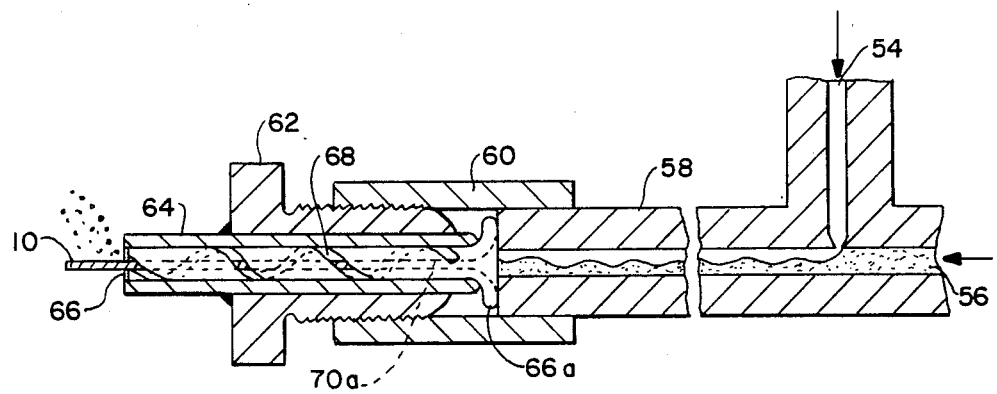
FIG.—3

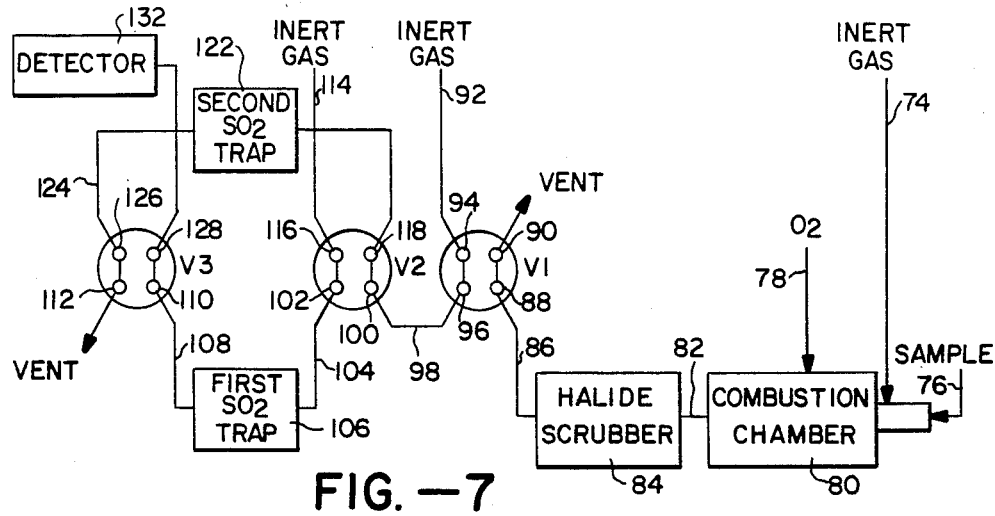
FIG.—7
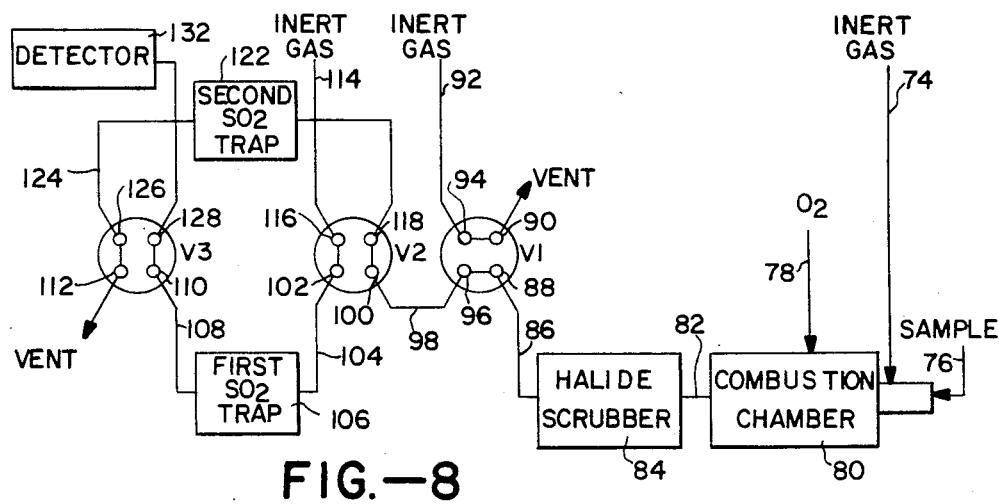
FIG.—8
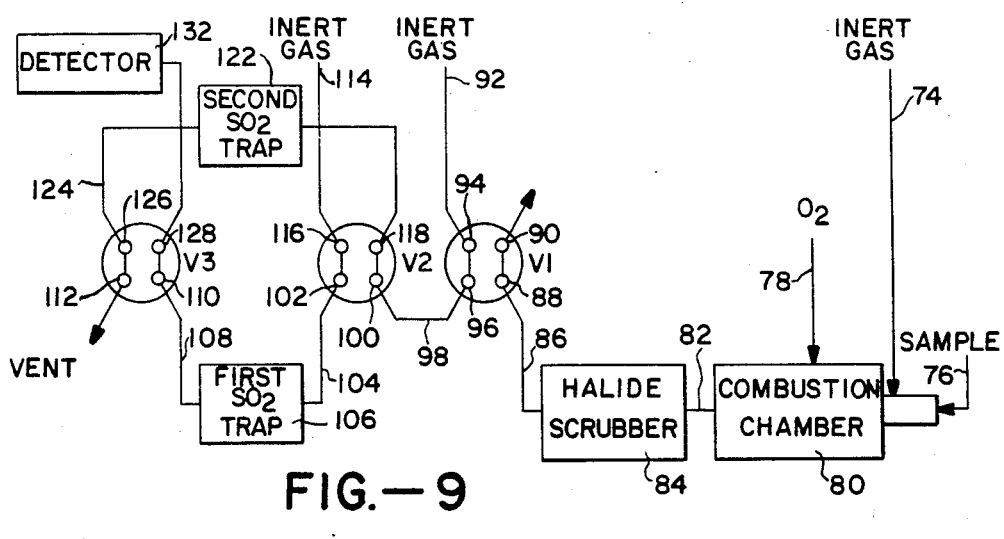
FIG.—9

SULFUR DIOXIDE ANALYSIS SYSTEM

BACKGROUND OF THE INVENTION

Various techniques have been utilized to remove sulfur dioxide from gas streams. For example, on an industrial basis, waste gases have been passed through a metal oxide medium in a sulfur oxide retention zone at a temperature in which the sulfur oxides are sorbed onto the medium. Thereafter, the medium may be regenerated by heating to a temperature at which the sulfur oxides are released. One such system is described in D'Souza et al U.S. Pat. No. 4,233,276. A survey of various metal oxides suitable for the above purpose is set out in Lowell et al, "Selection of Metal Oxides for Removing $SO_2$ from Flue Gas", Ind. Eng. Chem. Process Des. Develop., Vol. 10, No. 3, 1971, pp. 384–390. This article concludes that the most promising oxides are Al, Bi, Ce, Co, Cr, Cu, Fe, Hf, Ni, Sn, Th, Ti, V, U, Zn, and Zr.

In an analytical environment, the sulfur content of carbonaceous samples have been determined by gas chromatography followed by sulfur dioxide analysis, such as in a conductivity cell. In Cropper U.S. Pat. No. 4,120,659, the sample is combusted to form sulfur dioxide and then passed through a gas chromatography column in which the sulfur dioxide is separated on a packing comprising a silica gel at a first temperature on the order of 100° C. A carrier gas sweeps the column and passes the gases to the conductivity detector for analysis.

Another system for the analysis of sulfur has been suggested in Oita, I. J., "Determination of Sub-ppm Levels of Sulfur", Abstract 119, American Chemical Society, Las Vegas, Nev. Meeting (Aug. 27, 1980). There, the sulfur in liquids or solids is analyzed by combustion of the sample to form a sulfur dioxide-containing analysis stream, which is passed through a copper oxide trapping medium at 700° C. to trap the sulfur pyrolysis products as copper sulfate. After completion of combustion, the copper sulfate is heated to 900° C. to release the sulfur as sulfur dioxide.

The Oita system is subject to a number of disadvantages. At the temperature of sulfur oxide release, both sulfur dioxide and sulfur trioxide are formed in the oxygen-containing combustion gas which passes through the combustion zone. Thus, it is necessary to assume a certain ratio of sulfur dioxide to sulfur trioxide in order to calculate the sulfur content of the sample. It has been found that this ratio is about 50% and is not reproducible, leading to errors in analysis.

SUMMARY OF THE INVENTION AND OBJECTS

The sulfur dioxide analysis system of the present invention includes a first step of passing a sulfur dioxide-containing analysis gas stream through a trap zone containing a sulfur dioxide trapping medium formed of metals or metal oxides, preferably nickel oxide, and maintained at a first temperature to retain the sulfur dioxide, while passing the remainder of the gas stream. Typically, the original sample is a solid or a liquid containing sulfur, and the sulfur dioxide in the analysis gas stream is formed by oxidative pyrolysis of the sample. After trapping, flow of analysis gas stream through the trap zone is discontinued and a carrier gas is passed through it while the zone is heated to a second temperature at which essentially all trapped sulfur dioxide is released as sulfur dioxide, and the resulting gas is passed through a non-specific detector, e.g., a conductivity cell, or through a specific detector for sulfur dioxide, e.g., a coulometric titration cell. Halide in the analysis gas stream is preferably removed prior to trapping by passage through a scrubbing chamber containing aqueous liquid which absorbs the halide. In a preferred system, two sulfur dioxide traps are provided for two different samples. By suitable valving, sulfur dioxide is removed from the analysis gas stream on one trap isolated from the detector, while the sulfur dioxide previously retained on the other trap is released and detected. Then, the positions of the two traps are reversed.

BRIEF DESCRIPTION OF THE DRAWINGS

FIG. 1 is a schematic flow diagram of a system in accordance with the present invention, using a single sulfur dioxide trap with the valve in a trapping position.

FIG. 2 is a schematic representation of the system of FIG. 1, illustrating the valve in a sulfur dioxide release and detection mode.

FIG. 3 illustrates a unique conductivity cell useful as a detector in the system of the present invention.

FIGS. 4 through 9 are schematic flow diagrams of a system in accordance with the present invention using two sulfur dioxide traps, illustrating sequential step-by-step flow through the valving system.

DETAILED DESCRIPTION OF THE PREFERRED EMBODIMENTS

Figure 4:
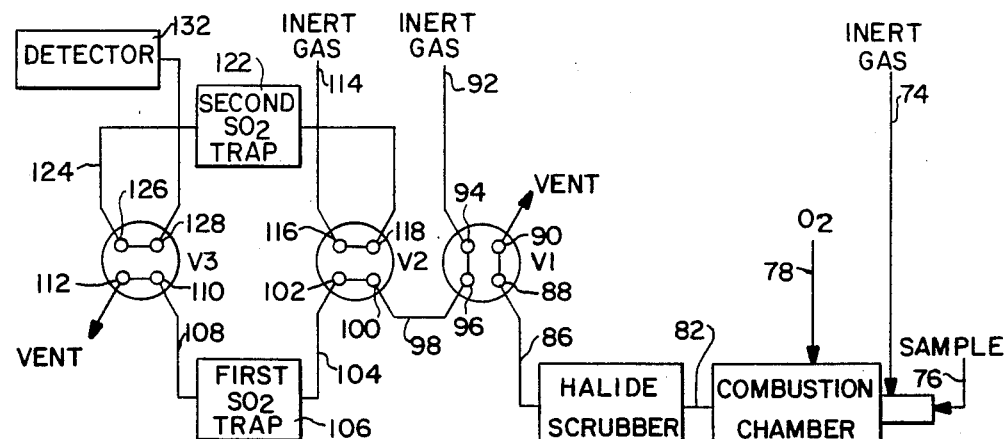

The system of FIGS. 1 and 2 is a single sulfur dioxide trap system, particularly adapted for analyzing the sulfur content of a liquid, for example gasoline, which is oxidatively pyrolyzed to form sulfur dioxide in the analysis gas. The concentration of the sulfur dioxide is quantitatively detected as a measure of the sulfur content in the liquid.

Referring to FIG. 1, the first step in the process is illustrated in which the sample is in liquid form and is injected as a liquid illustrated as source 10, typically through a syringe into a septum, not shown, into the inlet side of a combustion chamber 12. An inert gas, suitably nitrogen, from source 14 is also directed in line 15 to the inlet side of the chamber and carries the gas into the central portion of combustion chamber 12, which is also supplied with oxygen from source 16. Heating means, not shown, such as a furnace is provided to combust the sample in the presence of the oxygen to form combustion gases including sulfur dioxide. The details of a microcoulometric technique utilizing oxidative pyrolysis as the first step are set forth in Wallace, et al, "Comparison of Oxidative and Reductive Methods for the Microcoulometric Determinations of Sulfur in Hydrocarbons", Analytical Chemistry, Vol. 42, No. 3, March 1970, pp. 387–394. A suitable oxidative pyrolysis system is sold under the designation MCTS-30 System by Dohrmann Division of Xertex Corporation.

In the illustrated embodiment, a liquid sample is vaporized and oxidized to form an analysis gas stream in which the formed sulfur dioxide is determined as a measure of the sulfur in the liquid sample. It should be understood that the present system is also applicable to the direct analysis of sulfur dioxide in a gas stream, rather than as the product of oxidative pyrolysis. In that instance, the gas stream would be passed directly to the next step of the process. Also, the system is applicable to the analysis of a solid sample containing sulfur.

There, the sample would be placed in the combustion chamber in a boat or the like, rather than through a syringe, and would be oxidatively pyrolyzed in the same general manner as with respect to the liquid sample described above.

In the next stage, the sample is passed through halide retention means illustrated as a halide scrubber 18. Scrubber 18 may be mounted directly to combustion chamber 12 utilizing a sealing O-ring 20. It is in form of a generally cylindrical flowthrough tube. Means for heating scrubber 18 are provided comprising a resistance coil 22. Also, cooling means in the form of fan 24 is provided.

The function of the halide scrubber is to remove the halide, primarily hydrogen chloride, and halogen, primarily chlorine, from the analysis gas stream. An aqueous liquid, suitably water, is provided to the halide scrubber as water of combustion or from an independent source. The water condenses at room temperature on the inner surface of the empty tube. For a sample containing, for example, up to 20 micrograms of chloride, the sulfur dioxide can be quantitatively passed through the scrubber while retaining the chloride. It is preferable to have a relatively low pH level for the water, on the order of pH 2–4, so that the hydrogen halide is trapped while passing the sulfur dioxide. At higher pH levels, say on the order of pH 6–8, some sulfur dioxide may be trapped as well. Acid gases such as hydrogen chloride, or carbon dioxide formed during combustion, lower the pH level of the condensed moisture. Where little or no acid gases are present in the combustion effluent, an independent source of acid gas may be introduced in the form of a carbon dioxide carrier or the like.

During the trapping stage illustrated in FIG. 1, the analysis gas exiting from the combustion chamber is passed through the halide scrubber 18 maintained at a relatively low temperature, typically room temperature, by actuation of fan 24 to cool the combustion gases. When the valve is set to the position of FIG. 2 described below, the gases passing through the halide scrubber are vented and heater 22 is actuated to vaporize the liquid in the scrubber and remove it to waste. Thereafter, aqueous liquid is again supplied to the scrubber in the manner set forth above.

The reason for removing the halide gas is that in certain detection systems, such as conductivity detection, the halide can interfere with the analysis of the sulfur dioxide. While the above halide scrubber is particularly effective due to its ready regeneration, it should be understood that, if desired, other systems may be employed for the retention of halides. Such systems include the use of a halide scrubbing medium, such as silver wool, tin granules, or iron ammonium sulfate crystals. These media eventually become exhausted and require replacement. Also, for optimum results, a preconditioning procedure is employed. While such scrubbers are effective for relatively low halide concentrations, at higher halide levels, e.g. greater than 0.2 micrograms of halide in the sample, the frequency of replacement can be troublesome.

In FIG. 1, valve means 26 is illustrated including three sets of two-way ports. In the valve position illustrated in FIG. 1, analysis gas from scrubber 18 passes via line 25 through inlet port 28, outlet port 30, and into sulfur dioxide trap 32. From there, the stream passes via line 34 through inlet port 36, out outlet port 38, and to vent in line 40. In this manner, valve means 26 in the trap position serves to direct gas from sulfur dioxide trap 32 to vent, bypassing detector 50. During this stage of the process an inert carrier stream from source 14 is directed via line 42 through inlet port 44, outlet port 46, and through line 48 and into sulfur dioxide detector 50 to maintain a base line in detector 50 for the detection stage as illustrated in FIG. 2. In addition, the inert carrier through conduit 15 transports the vaporized sample to the oxidation zone.

Trap 32 comprises a flowthrough tube including a sulfur dioxide trapping medium comprised of metal, metal oxide, and mixtures of the same. A preferred form of trapping medium is a bed of inert particles coated with nickel, e.g., 10–20 mesh silica alumina coated with 10% nickel by weight, having an external layer less reactive with sulfur dioxide than the nickel metal. Nickel oxide is a preferable external layer. Without such an external layer, the sulfur dioxide may be so strongly bound by the nickel metal that part of it would not be released in the second stage.

Trap 32 functions by retaining the sulfur dioxide at a first predetermined temperature at which the trap is maintained in the flow scheme illustrated in FIG. 1. This temperature is selected to trap the sulfur dioxide while permitting passage of the remainder of the gases in the analysis stream. Thereafter, the valving is switched to pass an inert gas through the trap at a temperature at which oxygen and carbon dioxide are removed but not sulfur dioxide. Then, the trap is heated and the sulfur dioxide is released and the sulfur dioxide-containing carrier gas is passed through the detector. Typical trapping temperatures for a nickel oxide is on the order of 500° C., while a typical release temperature is on the order of 900° C. Such temperatures are substantially greater than 300° C., which is above the maximum temperature typically employed in silica gels or other gas chromatography media.

The mechanism of trapping has not been fully analyzed. However, it is believed that the sulfur dioxide is chemisorbed or enters into a chemical reaction with the metal or metal oxide, specifically nickel or nickel oxide. It is believed that the mechanism includes at least some chemisorption because trace amounts of the trapped sulfur dioxide will elute from the trapping medium if the trap is held at the trapping temperature for several hours.

Referring to FIG. 2, a system of the components of FIG. 1 is illustrated, with the position of valve means 26 shifted to the release position. As illustrated, valve means 26 includes two positions. In the trap position illustrated in FIG. 1, gas is passed from combustion chamber 12 through the sulfur dioxide trap, wherein the sulfur dioxide is retained on the trapping medium. The second position is illustrated in FIG. 2, in which flow is discontinued from the combustion chamber to the trapping means, and carrier gas is directed through the trapping means, wherein it picks up sulfur dioxide gas released there and carries it to the sulfur dioxide detector 50. The valve is actuated to the position of FIG. 2 when a sufficient amount of the sample has been combusted and carried in the analysis gas stream through the $SO_2$ trap.

After valve 26 is moved to the position of FIG. 2, and a sufficient amount of sample 10 has been combusted and passed through trap 32, fan 24 is deactuated and heating element 32 is actuated to heat scrubber 18 to a point at which all aqueous liquid containing the halides is vaporized and passed through ports 28 and 38 to vent.

In this manner, when the valve is again returned to the position of FIG. 1, the halide scrubber is cleaned of contaminants and the aqueous liquid may again be deposited in the scrubber to repeat the cycle.

Referring again to FIG. 2, inert gas from source 14 passes through ports 44 and 30, and then through trap 32 for a time sufficient to remove $CO_2$, $O_2$, nitrogen oxides, and other interfering species, typically 2 minutes. At the end of this 2 minute time, trap 32 is heated to a temperature at which the sulfur dioxide is released from the trapping medium, e.g. on the order of 900° C. The carrier gas containing the sulfur dioxide is then passed via line 34 through ports 36 and 46, and through sulfur dioxide detector 50, wherein the concentration of sulfur dioxide is determined as a measure of the sulfur originally contained in the sample.

A variety of detectors may be employed for detector 50. For example, detector 50 may be a coulometric detector of the type sold in the system designated MCTS 30 System, specifically the T300P cell of that system, sold by Dohrmann Division of Xertex Corporation. This system is based on an iodine/iodide reaction. Other analysis systems may be employed, including flame photometry, ultra-violet detection, fluorescence detection, and solid state transducers responsive to sulfur dioxide.

Conductivity detectors have been used in gas chromatography systems, e.g. as described in R. C. Hall, "A Highly Sensitive and Selective Microelectrolytic Conductivity Detector for Gas Chromatography", Journal of Chromatographic Science, Vol. 12, March 1974, pp. 152–160. In that type of system, the sulfur dioxide-containing gas is mixed with water to form sulfurous acid, and is passed through gas capillaries to remove the remainder of the gas from the liquid, taking care to avoid gas bubbles in the remaining liquid. Then, the liquid is passed through a conductivity cell in which spaced electrodes measure the conductivity of the liquid, which is proportional to the amount of sulfur dioxide present in the original gas stream. One problem with this system is that any gas bubbles present in the liquid interferes with the accurate quantitation of the sulfur dioxide.

Referring to FIG. 3, a conductivity detector is illustrated which is particularly suitable for the analysis of sulfur dioxide or other gas which forms a conductive liquid. Specifically, the sulfur dioxide in the gas stream is contacted with water to form aqueous sulfurous acid solution, which is then passed through a conductivity cell. The conductivity of the acid solution is detected as a measure of the quantity of sulfur dioxide in the gas stream. The sulfurous acid solution and gas stream are passed simultaneously through the conductivity cell without prior separation of the gas stream and sulfurous acid solution, as performed in known systems.

Referring to the specific embodiment of FIG. 3, the system includes an inlet member 52 defining a gas inlet conduit with a constricted interior and communicating with a liquid inlet conduit 56 in a T-type of connection for contact at a substantial angle (e.g., right angle). To the downstream side of this connection is an elongate conduit 58, partially broken away, wherein the gas and liquid mix and contact each other. A suitable size for conduit 58 is a glass capillary with 1 mm inner diameter and 6 mm outer diameter. The downstream end of conduit 58 fits within the interior of a connecting member 60. A tight fit is provided suitably by press-fitting and an adhesive. A hollow fitting 62 is received at the other end of connector 60 by threaded connection. To the interior of fitting 62 is an electrode in the form of hollow cylindrical metallic tube 64, surrounding a flared electrically insulative tube 66, which forms a gas tight seal at its flared end 66a with conduit 58. Interior of tube 66 is a hollow spiral ribbon 68, formed of an electrically insulative material such as teflon, which surrounds an inner electrode rod 70, which rods extend from the downstream free end of tube 66 inwardly to its interior end 70a.

The flowthrough conductivity detector of FIG. 3 defines a spiral slot wherein the liquid and gas pass simultaneously between electrodes 64 and 70 in the spiral opening, providing substantial turbulence throughout the passage to assure continuous intimate mixing of liquid and gas and thereby yielding a relatively constant response for high accuracy averaged over a period of time. This is to be contrasted with conductivity cells of the prior art in which there is an attempted separation of the gas and liquid, and only the liquid passes through the cell. In such prior art devices, the presence of gas bubbles can lead to substantial detection errors.

In operation of the conductivity detector, the carrier gas containing the sulfur dioxide passes through conduit 54 and is mixed with water provided in conduit 56 in right angle contact to produce substantial turbulence and mixing, resulting in the formation of sulfur dioxide with the liquid forming a fine mist. This liquid gas mixture is then passed through the funnel-shaped opening within flared end 66a of tube 66. The fine mist formed creates uniform pulses. The mist is passed in the spiral opening provided to the interior of that tube along spiral ribbon 68, wherein the average conductivity is measured between electrodes 64 and 70. After passage through the conductivity cell, the gas liquid mixture is vented.

Referring to FIGS. 4–9, an embodiment of the system is illustrated wherein two sulfur dioxide traps are employed with a single detector. In this manner, as set forth below, two samples may be analyzed using a single detector in one-half the analysis time which would be required if only a single sulfur dioxide trap is employed. In the illustrated embodiment, in addition to the two traps, other differences from the embodiment of FIGS. 1 and 2 include a second source of inert or purge gas, and three valves with six different synchronous positions. However, it should be understood that another valving system may be employed so long as it serves the functions set out below.

For simplicity of description, the system will first be described with reference to the step-by-step procedures set out in the drawings. It should be understood that the starting point of the sequence is not significant so long as the illustrated order is employed.

Referring to FIG. 4 (step 1), inert gas from a source 74 and sample from a source 76 and oxygen from a source 78 are passed into a combustion chamber 80 of the same type as chamber 12 described above. It is assumed that the sample is injected as a liquid through a syringe into the inlet side of the chamber. A conduit 82 interconnects combustion chamber 80 and halide scrubber 84, of the same type as scrubber 18 described above, and the gas from scrubber 84 is directed through line 86 into port 88 of valve V1, and out port 90 to vent. The valve assembly or means described herein includes the functions of valves V1, V2 and V3. An inert gas, e.g. nitrogen, from a source 92 is directed into port 94 and out port 96 of valve V1, through line 98 into port 100 of valve V2 and out port 102 through line 104, and through the first sulfur dioxide trap, designated 106. Trap 106 is connected by a line 108 to port 110 of valve V3, which is in turn connected to port 112, passing the gas contained therein from trap 106 to vent. Another gas stream from source 114 is directed into port 116 and out port 118 of valve V2, out port 118 by a line 120 through the second sulfur dioxide trap, designated 122, out line 124 through ports 126 and 128 of valve V2, and through line 130 to detector 132. Traps 1 and 2 are of the type designated as trap 32 in the embodiment of FIGS. 1 and 2, while detector 132 is of the type described as detector 50 in the same embodiment.

In step 1, the needle of the sample syringe is passed through the septum at the inlet of the combustion chamber to introduce a needle blank, during which procedure it is possible to introduce contaminants into the combustion gas. Such contaminants are passed by the gas streams through valve V1 and to vent. The halide scrubber is unheated during this stage of the cycle. Inert gas from source 92 is directed through trap 106 to vent, while inert gas from source 114 is directed through trap 122 to the detector. At this stage of the cycle, sulfur dioxide, which has previously been retained by trap 122, is released in the inert gas by heating the trap to 900° C. The inert gas is then passed to the detector. At this time, the inert gas from source 92 passing through trap 106 facilitates the synchronous use of a three-valve system, but is not functionally necessary.

Figure 5:
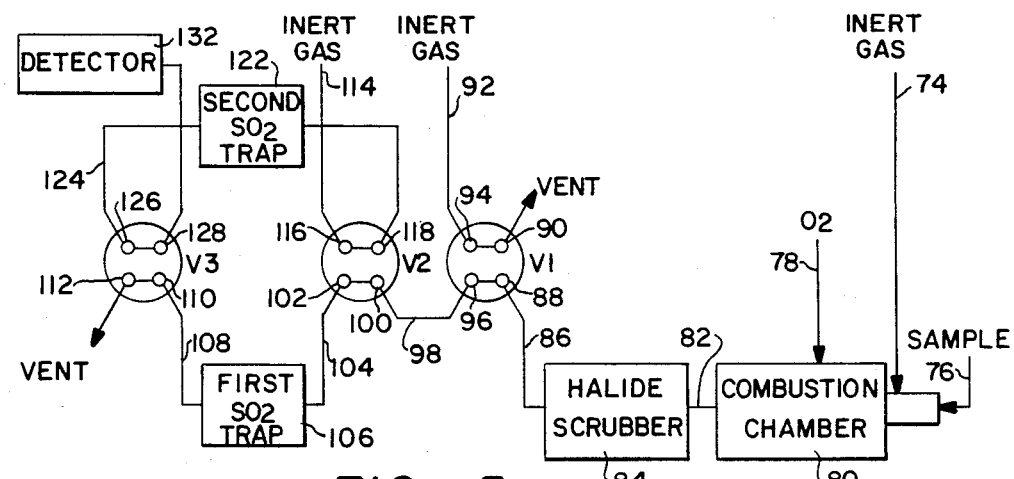

After approximately one minute at the setting illustrated in FIG. 4, the valves are switched to the position illustrated in FIG. 5 (step 2 of the operational sequence). The sample in the combustion chamber is oxidatively pyrolyzed and passed into the halide scrubber, which has previously been provided with an acidic water solution, now maintained at room temperature. The halide is retained in the solution, while the remainder of the analysis stream is passed through valves V1 and V2 and into trap 106, maintained at the trapping temperature of 500° C. Thereafter, the analysis gas passes through valve V3 to vent. The valves are retained in the setting of step 2 for approximately 90 seconds, which is sufficient time to oxidatively pyrolyze the sample and to trap the sulfur dioxide in trap 106.

Figure 6:
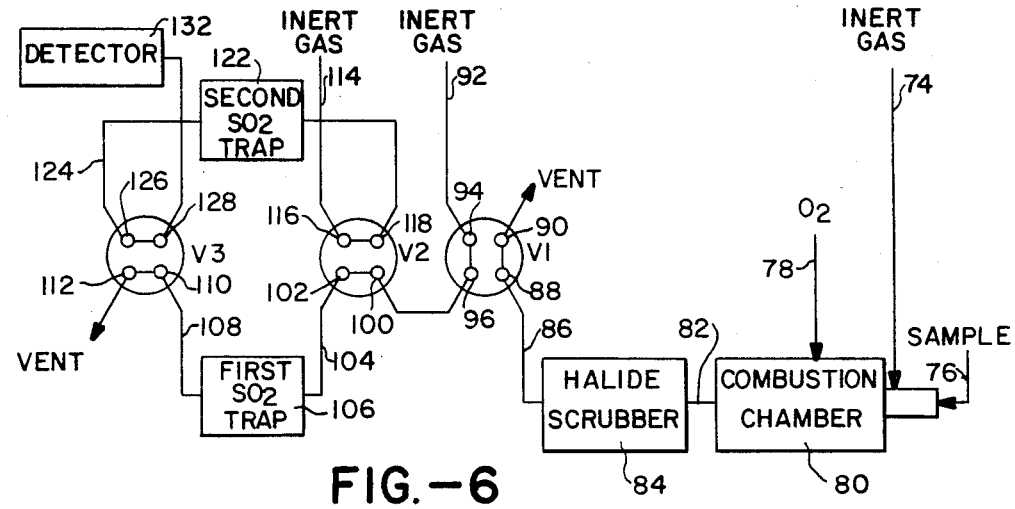

After completion of step 2, valve V1 is switched back to the position illustrated in FIG. 6 (step 3). The gases from the combustion chamber are vented, inert gas is passed through trap 106 from source 92 and to vent, thereby sweeping trap 106 of carbon dioxide, oxygen, and other undesirable combustion products. At this time, the halide scrubber is heated to vaporize the halide-containing liquid and pass it to vent. The valves are maintained in this position for approximately 90 seconds. The total elapsed time for steps 1, 2 and 3 is approximately four minutes.

In steps 1, 2 and 3, valves V2 and V3 are not switched and inert gas from source 114 passes continuously through valve V2, through trap 122, and into the detector. Sulfur dioxide previously trapped in trap 122 is quantitatively analyzed by the detector during steps 1, 2 and 3, wherein at least a portion of the time the temperature of trap 122 is elevated to about 900° C. to release the sulfur dioxide from the trap. The sulfur dioxide on trap 122 has previously been trapped there, as explained below.

Referring to FIG. 7, step 4 in the procedure, valve V1 is maintained in the same position as in step 3, while valves V2 and V3 are switched together. Here, inert gas from source 114 is passed through valve V2, trap 106, valve V3 and through the detector. During this time, the temperature of trap 106 is elevated to 900° C., at which the sulfur dioxide is released for detection in the detector. This position of valves V2 and V3 is maintained during steps 5 and 6, as illustrated in FIGS. 8 and 9, respectively. During step 4, the needle blank from the combustion chamber is passed through valve V1 to vent, as described above.

At the end of step 4, valve V1 is switched so that the sample in combustion chamber 80 is directed through the halide scrubber 84, valve V1, valve V2, and into trap 122, maintained at a sulfur dioxide trapping temperature, and from there through valve V3 to vent. During this time, the sulfur dioxide in the gas produced in the combustion chamber is trapped in trap 122.

Thereafter, in step 6, illustrated in FIG. 9, inert gas from source 92 is directed through valves V1 and V2 through trap 122 to vent, to sweep the trap of carbon dioxide, oxygen, and other undesirable combustion products in the trap prior to release of the sulfur dioxide from the trap.

It is apparent that in the foregoing system, there is a doubling of the number of samples that can be analyzed by a single detector. Thus, whereas approximately 8 minutes is required for a single trap system, as set forth in FIGS. 1 and 2, only 4 minutes would be required by use of the dual trap system.

The system illustrated in FIGS. 4–9 illustrates a dual-trap system, together with a combustion chamber for the sample to be analyzed. In a broad sense, the present system contemplates passing a sulfur dioxide-containing analysis gas stream from any source through a sulfur dioxide trapping medium in a first trap zone, maintained at a first predetermined temperature to retain the sulfur dioxide on the trapping medium while passing the remainder of the gas stream. Then, the analysis gas stream flow through the first trap zone is discontinued and the first trap zone is heated to a second predetermined temperature at which the sulfur dioxide is released from the trapping medium in a carrier gas stream. Thereafter, the sulfur dioxide-containing carrier gas stream from the previous step is passed through a sulfur dioxide detector, and the concentration of sulfur dioxide is determined. After discontinuing flow of the analysis gas stream through the first trap zone, and before terminating detection, a sulfur dioxide analysis gas stream is passed through a second trap zone wherein the sulfur dioxide is retained, then the analysis gas stream is discontinued in the second trap zone and, during at least a portion of the trapping in the first trap zone, the second trap zone is heated and the sulfur dioxide is released and passed through the detector.

While a three-valve system is illustrated in FIGS. 4–9, it is understood that other valve means which can accomplish the above functions can be employed. Thus, the valve means of the present invention has a first trap position serving, when selected, to direct gas from a sulfur dioxide-containing gas supply to a first trap. The valve means also includes a first release position serving, when selected, to discontinue flow from the sulfur dioxide-containing gas supply means through the first trap, to direct carrier gas from the carrier gas supply means through the first trap, and to direct sulfur dioxide gas released there through the sulfur dioxide detection means. The valve means also includes a second trap position serving, when selected, to direct gas from a sulfur dioxide-containing gas supply means to the second trap. In addition, the valve means includes a second release position serving, when selected, to discontinue flow from the sulfur dioxide-containing gas supply means to the second trap, to direct carrier gas from the carrier gas supply means through the second trap, and to direct sulfur dioxide gas released there through the sulfur dioxide detection means. The first trap position is operable synchronously with the second release position, while the second trap position is operable synchronously with the first release position. In this manner, capacity of the system is doubled compared to a single trap system.

A further disclosure of the nature of the present invention is provided by the following specific examples of the practice of the same. It should be understood that the data disclosed serve only as examples and are not intended to limit the scope of the invention.

EXAMPLE 1

The apparatus illustrated in FIGS. 1, 2, and 3 was utilized to measure the sulfur content of a sample of iso-octane containing 0.1 ppm sulfur. The trapping medium for the $SO_2$ trap comprised 10% nickel coated onto silica alumina particles (10–20 mesh) oxidized at 850° C. for 30 minutes. The system parameters were established as follows:

Inlet $N_2$ flow 50 cc/min (conduit 15)
$O_2$ flow 250 cc/min (conduit 16)
Detector $N_2$ flow 100 cc/min (conduit 42)
Inlet temp. 750° C.
Combustion temp. 850° C.
$SO_2$ trap
   500° C. $SO_2$ trap temp.
   850° C. $SO_2$ release temp.
$H_2O$ flow 0.5 ml/min (conduit 56, FIG. 3)
Halide scrubber: room temperature for halide retention; 200° C. for venting $H_2O$+halide Leeds & Northrup conductivity detector Model 70775-1-011, modified as follows. The detector included a 1 inch length, 0.125 inch diameter s.s. tubing insulated from a co-axial 0.03 inch diameter s.s. rod by thin wall 0.0625 inch teflon tubing with a flare on one end and a thin spiral slit traversing the length of the tube except for a portion near the flared end.

Valve: Rheodyne, Inc. 6 port/3 way teflon valve.

At the beginning of the analysis cycle (t=0) the system is in the configuration of FIG. 2. The needle of a 500 μl syringe containing the sample is inserted through the inlet septum into the inlet where any residual sulfur is driven off the needle to vent, constituting the "needle blank". At t=30 seconds, 20 μl (of $H_2O$ is injected into the oxygen flow (conduit 16) and predeposits on the walls of the chloride scrubber. At t=60 seconds, the valve is switched to the configuration of FIG. 1 and the syringe drive is started, injecting the sample at a rate of 1 μl/sec. Inert gas (nitrogen) in line 15 sweeps the vaporized sample on to the combustion zone, where the sample is combusted to $CO_2$, $H_2O$, $SO_2$, $SO_3$, various acid halide gases (HCl, HOCl, $Cl_2$), various nitrogen oxides (NO, $NO_2$, $N_2O_3$), etc. The water of combustion joins the predeposited water on the walls of the chloride scrubber, and scrubs the halide gases and the $SO_3$ from the combustion effluent, passing the $SO_2$ and the remaining gas on to the sulfur trap. The $SO_2$ is retained on the sulfur trap while the remainder of the pyrolysis products pass on to vent.

At t=150 seconds, sample injection is halted and the furnace oxygen and nitrogen push the final products of combustion on through the chloride trap, through the $SO_2$ trap, and on to vent. At t=270 seconds, the valve is switched to the release position shown in FIG. 2, and 100 cc/min. of nitrogen carrier gas flow (conduit 42) sweep the oxygen, residual $CO_2$, and residual $NO_x$ through the detector, causing a purge peak, since the conductivity detector responds to $NO_x$ and $CO_2$ (as it does to $SO_2$). At t=390 seconds, the temperature of the $SO_2$ trap is raised to 850° C. at a 10° C./second rate by means of heater windings similar to those on the chloride scrubber, the $SO_2$ is quantitatively released (>95%) and carried to the conductivity detector, causing a sharp $SO_2$ peak on the trailing edge of the $CO_2$ peak. The millivolt-seconds (mv-sec) area under this peak is proportional to the sulfur content of the original sample and is integrated by conventional means. The $SO_2$ concentration in the original sample is determined by comparing the peak area obtained on the present sample to the area generated by a 1 ppm sulfur standard previously analyzed. Detector sensitivity is typically 2500 mv-sec/ppm for a 90 μl sample, with a precision of +/−20 mv-sec or +/−2% of the reading, whichever is greater. This calculates to a precision of +/−0.008 ppm sulfur in the original sample. Integration time was set at 80 seconds.

EXAMPLE 2

In the two trap arrangement, FIGS. 4–9, the components and system parameters were identical to those described above except for the valve arrangement, the extra trap, and the extra gas flow (conduit 114).

Slight differences in timing and operation are permitted due to the additional components: At t=30 seconds, sample injet is begun and $H_2O$ is *not* predeposited; at t=60 seconds, only valve $V_1$ is switched to the FIG. 5 configuration to effect the $SO_2$ trapping. At t=150 seconds, valve $V_1$ is switched back to the FIG. 6 configuration to end the trap period. Then the chloride trap is heated to vent $H_2O$ and trapped halides. At t=240 seconds, valves $V_2$ and $V_3$ are switched together to the FIG. 7 configuration, which constitutes the release mode of the analytical cycle. Considerations for the release mode are similar to those described in the sample trap case, except that a subsequent sample may be trapped on the alternate trap (second trap, FIGS. 8 and 9), while the previously trapped $SO_2$ is being released from the first trap.

What is claimed is:

1. In a method for the quantitative detection of sulfur dioxide in a gas stream, the steps of:
    (a) passing a sulfur dioxide-containing analysis gas stream through a sulfur dioxide trapping medium comprising nickel oxide, in a trap zone maintained at a predetermined temperature to retain the sulfur dioxide on the trapping medium while passing the remainder of the gas stream,
    (b) discontinuing flow of the analysis gas stream through the trap zone,
    (c) thereafter heating the trap zone to a second predetermined temperature at which the sulfur dioxide is released from said trapping medium and passing a carrier gas stream through said trap zone to carry away said released sulfur dioxide, said carrier gas stream being substantially inert to sulfur dioxide at said second predetermined temperature, and (d) passing said sulfur dioxide-containing carrier gas stream through a sulfur dioxide detector and determining the concentration of sulfur dioxide therein.

2. In a method for the quantitative detection of sulfur dioxide in a gas stream, the steps of:
(a) passing a sulfur dioxide-containing analysis gas stream through a sulfur dioxide trapping medium comprising a nickel metal substrate with an external layer comprising nickel oxide in a trap zone maintained at a predetermined temperature to retain the sulfur dioxide on the trapping medium while passing the remainder of the gas stream,
(b) discontinuing flow of the analysis gas stream through the trap zone,
(c) thereafter heating the trap zone to a second predetermined temperature at which the sulfur dioxide is released from said trapping medium and passing a carrier gas stream through said trap zone to carry away said released sulfur dioxide, said carrier gas stream being substantially inert to sulfur dioxide at said second predetermined temperature, and
(d) passing said sulfur dioxide-containing carrier gas stream through a sulfur dioxide detector and determining the concentration of sulfur dioxide therein.

3. The method of claims 1 or 2 together with the step of oxidatively pyrolyzing a sulfur-containing sample to form the sulfur dioxide-containing analysis gas stream.

4. The method of claims 1 or 2 in which in step (a), the trapping medium is maintained at a temperature greater than 400° C.

5. The method of claims 1 or 2 in which said sulfur dioxide-containing carrier gas stream is contacted with water so that said sulfur dioxide forms sulfurous acid and the detection step is performed by measurement of the sulfurous acid conductivity in a conductivity cell.

6. The method of claim 5 in which there is no separation of the sulfurous acid and carrier gas stream prior to passage through the conductivity cell.

7. The method of claims 1 or 2 in which the analysis gas stream contains halide gas and including the additional step of:
(e) prior to step (a), removing the halide gas from the analysis gas stream.

8. The method of claim 7 in which the halide gas is removed by passing the analysis gas stream through a scrubbing chamber containing an aqueous liquid on a wall thereof and dissolving the halide in the aqueous liquid while passing the sulfur dioxide in the analysis gas stream.

9. The method of claim 8 in which after completion of steps (a) and (e), the scrubbing chamber is purged by heating it to vaporize the halide-containing aqueous solution, and passing a gas stream through the scrubbing chamber to vent the thus-formed vapor therefrom.

* * * * *